US010906862B2

(12) United States Patent
Lang et al.

(10) Patent No.: US 10,906,862 B2
(45) Date of Patent: *Feb. 2, 2021

(54) PROCESS FOR ISOLATING PURE BUTYL ACRYLATE FROM CRUDE BUTYL ACRYLATE BY DISTILLATION, WHERE BUTYL IS N-BUTYL OR ISOBUTYL

(71) Applicant: BASF SE, Ludwigshafen am Rhein (DE)

(72) Inventors: Ortmund Lang, Ludwigshafen (DE); Bernd Metzen, Ludwigshafen (DE); Claus Hechler, Ludwigshafen (DE)

(73) Assignee: BASF SE, Ludwigshafen am Rhein (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/472,018

(22) PCT Filed: Dec. 11, 2017

(86) PCT No.: PCT/EP2017/082186
§ 371 (c)(1),
(2) Date: Jun. 20, 2019

(87) PCT Pub. No.: WO2018/114422
PCT Pub. Date: Jun. 28, 2018

(65) Prior Publication Data
US 2020/0095185 A1    Mar. 26, 2020

(30) Foreign Application Priority Data
Dec. 21, 2016  (EP) .................... 16205953

(51) Int. Cl.
| | | |
|---|---|---|
| C07C 67/54 | (2006.01) | |
| B01D 3/14 | (2006.01) | |
| B01D 3/42 | (2006.01) | |
| C07C 69/54 | (2006.01) | |

(52) U.S. Cl.
CPC .............. *C07C 67/54* (2013.01); *B01D 3/141* (2013.01); *B01D 3/148* (2013.01); *B01D 3/42* (2013.01); *C07C 69/54* (2013.01)

(58) Field of Classification Search
CPC ......... C07C 67/54; C07C 69/54; B01D 3/141; B01D 3/148; B01D 3/42
See application file for complete search history.

(56) References Cited

U.S. PATENT DOCUMENTS

| | | | | |
|---|---|---|---|---|
| 7,520,964 B2 * | 4/2009 | Hammon | ................ | C07C 51/44 |
| | | | | 562/600 |
| 2013/0284586 A1 * | 10/2013 | Lee | ........................ | B01D 3/141 |
| | | | | 203/99 |
| 2018/0361270 A1 | 12/2018 | Asprion | | |
| 2019/0016665 A1 | 1/2019 | Tretjak et al. | | |

FOREIGN PATENT DOCUMENTS

| | | |
|---|---|---|
| DE | 33 02 525 A1 | 7/1984 |
| DE | 102 58 329 A1 | 7/2003 |
| DE | 10 2005 053 982 A1 | 5/2006 |
| JP | 2005-239564 * | 9/2005 |
| JP | 2005-239564 A | 9/2005 |
| WO | WO 03/043712 A1 | 5/2003 |
| WO | WO 2017/125657 A1 | 7/2017 |

OTHER PUBLICATIONS

JP 2005-239564 translated (Year: 2005).*
(Arjomand Scientia Iranica, Transactions C: Chemistry and Chemical Engineering, 22(6) 2015, p. 2358-2372) (Year: 2015).*
U.S. Appl. No. 16/468,823, filed Jun. 12, 2019, Ortmund Lang.
U.S. Appl. No. 16/471,993, filed Jun. 20, 2019, Ortmund Lang.
U.S. Appl. No. 16/472,054, filed Jun. 20, 2019, Ortmund Lang.
Extended European Search Report dated Jun. 26, 2017 in Patent Application No. 16205953.9.
Kaibel, G. "Distillation Columns with Vertical Partitions" Chemical Engineering Technology, vol. 10, No. 1, 1987, pp. 92-98.
Becker, H. "Polymerisationsinhibierung von (Meth-)Acrylaten", Fachbereich Chemie Technische Universität, 2003, 236 pages (with English abstract).
Kaibel, G. et al. "Möglichkeiten zur Prozeßintegration bei destillativen Trennverfahren" Chemie Ingenieur Technik, vol. 61, No. 2, 1989, pp. 104-112 (with English abstract).
International Search Report dated Feb. 19, 2018 in PCT/EP2017/082186, citing document AP therein, 2 pages.

* cited by examiner

*Primary Examiner* — Yevgeny Valenrod
*Assistant Examiner* — Blaine G Doletski
(74) *Attorney, Agent, or Firm* — Oblon, McClelland, Maier & Neustadt, L.L.P.

(57) ABSTRACT

A process for isolating pure butyl acrylate from crude butyl acrylate, which is carried out in a dividing wall column having separation-active internals and a vaporizer, and in which: a dividing wall is arranged in a longitudinal direction of the column to form an upper joint column region, a lower joint column region, an inflow section having a side feed point and an offtake section having a side offtake point; ratio of an amount of liquid at an upper end of the dividing wall going to an enrichment section and a stripping section of the column is set in the range from 1:0.2 to 1:5; and a ratio of an amount of vapor streams at a lower end of the dividing wall going to the stripping section and the enrichment section of the column is set in a range from 1:0.5 to 1:2.0.

22 Claims, 2 Drawing Sheets

PROCESS FOR ISOLATING PURE BUTYL ACRYLATE FROM CRUDE BUTYL ACRYLATE BY DISTILLATION, WHERE BUTYL IS N-BUTYL OR ISOBUTYL

Esters of acrylic acid, $H_2C=CH-C(=O)OR$, will hereinafter also be referred to as acrylates. R is an alkyl radical.

Acrylates such as n-butyl acrylate are generally obtained industrially by reaction of alcohol (example: n-butanol) and acrylic acid. The synthesis (esterification reaction) forms a product mixture, also referred to as crude acrylate, in which the acrylate generally predominates.

Acrylates of interest are n-butyl acrylate and isobutyl acrylate. Thus, R corresponds to n-butyl or isobutyl.

Butyl acrylates are employed for surface coatings, adhesives, building chemicals, paper coatings and plastics.

In order to meet specification requirements, the crude acrylate obtained in a synthesis has to be purified further by distillation. The specification requirements for pure acrylates provide in particular for, for example, a minimum content of acrylate of 99.5% by weight and a maximum permissible content of acetate, $RO(C=O)CH_3$, of 1500 ppm and of diether, ROR, of 1000 ppm. The isolation of acrylate from the crude acrylate is a complicated distillation problem because of the small differences in the relative volatilities of the components and is therefore generally carried out by means of a two-column arrangement (see below). Owing to the sensitivity of the polymerization-prone acrylates, particular column internals are generally particularly advantageous.

The isolation of acrylate from crude acrylate by distillation is, after a pre-purification which is preferably carried out, e.g. by extraction, carried out in the prior art as is presented, for example, in the thesis "Polymerisationsinhibierung von (Meth-)Acrylaten", TU Darmstadt (Chemistry department), 2003, by Holger Becker on pages 21 to 24 in two distillation columns connected in series:

In a first distillation column, a mixture of predominantly low boilers (relative to the butyl acrylate), e.g., water, alcohol (ROH), acetate ($RO(C=O)CH_3$), diether (ROR), is taken off as overhead product, with the organic low boilers being able to be recirculated to the esterification. At the bottom, the acrylate and the relatively high boilers are separated off. In a second downstream distillation column, the relatively high boilers (relative to the butyl acrylate), e.g. butoxy ester ($ROCH_2CH_2C(=O)OR$), are separated off as bottom product. The desired product (i.e. the pure butyl acrylate) is taken off as overhead product from the second distillation column; cf. columns H and I in FIGS. 3-7 on page 24 of the abovementioned thesis. The bottom output from column I is fed to a high boiler separator J (cf. FIGS. 3-7 on page 24 of the abovementioned thesis).

DE 3302525 A1 (BASF AG) and the specialist literature, for example Kaibel et al. in Chem. Eng. Technol. 10 (1987), pages 92 to 98, and in Chem. Ing.-Tech. 61 (1989), No. 2, pages 104 to 112, describe in general terms the use of dividing wall columns in the purification of organic compounds by distillation.

US 2013/0284586 A1 (LG Chem. Ltd.) describes the use of a dividing wall column for purifying 2-ethylhexyl acrylate by distillation.

JP 2005/239564 A (Mitsubishi Rayon Co.) describes the distillation of (meth)acrylic esters using a dividing wall column.

Figure 1:
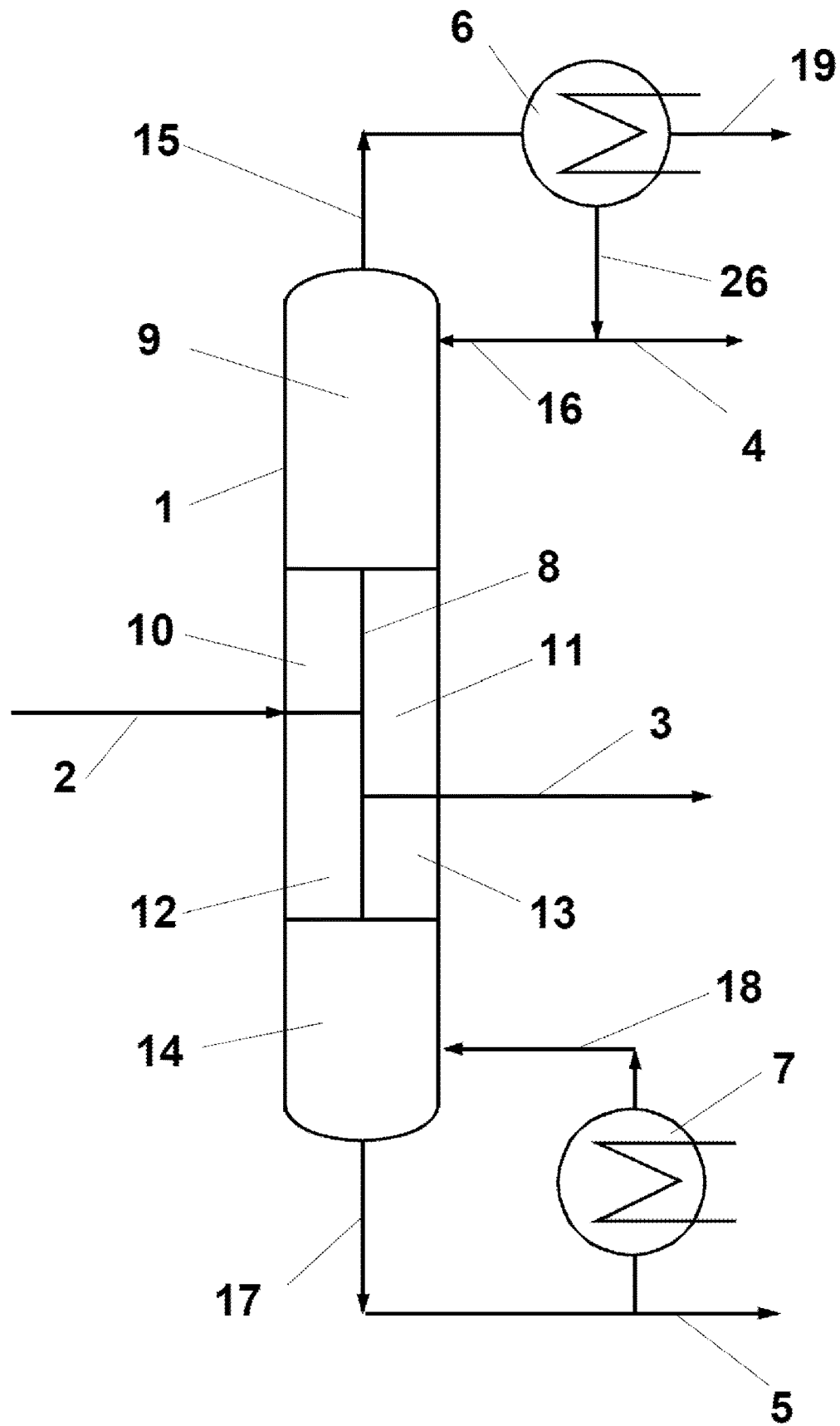
FIG. 1 shows a dividing wall column having a dividing wall which divides the dividing wall column into a joint upper column region, an inflow section and with enrichment section and stripping section, an offtake section with a stripping section and an enrichment section, and also a joint lower column region.

In the light of this literature, it was an object of the invention to provide an improved process for the isolation of pure butyl acrylate, namely n-butyl and isobutyl acrylate, from the corresponding crude butyl acrylate by distillation, which process is, while adhering to the respective specifications for the pure butyl acrylate, more economical, in particular in respect of the capital costs and energy costs.

We have accordingly found a process for isolating pure butyl acrylate from crude butyl acrylate, where butyl is n-butyl or isobutyl, by distillation, wherein the process is carried out in a dividing wall column (1) which has separation-active internals and vaporizer (7) and in which a dividing wall (8) is arranged in the longitudinal direction of the column to form an upper joint column region (9), a lower joint column region (14), an inflow section (10, 12) having a side feed point (2) and an offtake section (11, 13) having a side offtake point (3), the column has a number of theoretical plates in the range from 20 to 80, the side feed point (2) for the crude butyl acrylate is arranged at a theoretical plate in the region commencing at least two theoretical plates above the bottommost theoretical plate and ending at least two theoretical plates below the uppermost theoretical plate, the side offtake point (3) for the pure butyl acrylate is arranged at a theoretical plate in the region commencing at least two theoretical plates above the bottommost theoretical plate and ending at least two theoretical plates below the uppermost theoretical plate and the dividing wall (8) is arranged in the column in the region commencing at least one theoretical plate above the bottommost theoretical plate and ending at least one theoretical plate below the uppermost theoretical plate.

For the purposes of the present invention, pure butyl acrylate is, in particular, a butyl acrylate having a purity of ≥98.5% by weight, in particular 99.5% by weight, of n-butyl acrylate or isobutyl acrylate.

For the purposes of the present invention, crude butyl acrylate is, in particular, a mixture having a content of butyl acrylate of from ≥40% by weight to ≤90% by weight, in particular from ≥60% by weight to ≤90% by weight, of n-butyl acrylate or isobutyl acrylate.

The crude n-butyl acrylate used in the process of the invention has, in particular, the following composition:
from 40 to 90% by weight, in particular from 60 to 90% by weight, of n-butyl acrylate,
from 0.1 to 20% by weight, in particular from 1 to 10% by weight, of n-butanol,
from 0.1 to 20% by weight, in particular from 0.5 to 10% by weight, of water,
from 0.1 to 20% by weight, in particular from 1 to 10% by weight, of relatively high boilers (relative to n-butyl acrylate),
from 0.1 to 20% by weight, in particular from 1 to 10% by weight, of further low boilers (relative to n-butyl acrylate).

The crude isobutyl acrylate used in the process of the invention has, in particular, the following composition:
from 40 to 90% by weight, in particular from 60 to 90% by weight, of isobutyl acrylate,
from 0.1 to 20% by weight, in particular from 1 to 10% by weight, of isobutanol,
from 0.1 to 20% by weight, in particular from 0.5 to 10% by weight, of water, from 0.1 to 20% by weight, in particular from 1 to 10% by weight, of relatively high boilers (relative to isobutyl acrylate), from 0.1 to 20% by weight, in particular from 1 to 10% by weight, of further low boilers (relative to isobutyl acrylate).

The process of the invention is carried out in a dividing wall column (1) in which a dividing wall (8) is arranged in the longitudinal direction of the column to form an upper joint column region (9), a lower joint column region (14), an inflow section (10, 12) and an offtake section (11, 13).

It has surprisingly been found that the isolation of pure butyl acrylate from crude butyl acrylate by distillation can, contrary to the assumption that a two-stage mode of operation at different pressures is necessary, be carried out in a single column, namely a dividing wall column, and thus at a uniform pressure.

A dividing wall column is a distillation column having a vertical dividing wall which, in subregions, prevents transverse mixing of liquid and vapor streams. The dividing wall, which generally consists of a flat metal sheet and can be welded, screwed or pushed in, divides the column in the longitudinal direction in its middle region into an inflow part and an offtake part.

The mixture to be fractionated, namely the crude butyl acrylate, is fed into the inflow section and the product, namely the pure butyl acrylate, is taken off from the offtake section.

The process is preferably carried out continuously.

The dividing wall column is, like generally any distillation column, equipped with a vaporizer (bottom vaporizer) (7) and a condenser (6) at the top of the column.

In the process of the invention, the residence time in the vaporizer (7) and the associated piping system is advantageously and preferably limited to from 1 to 60 minutes, more preferably to from 10 to 30 minutes. This ensures trouble-free operation of the plant, in particular only little or no fouling, despite the polymerization susceptibility of the mixture.

In a preferred process variant, the ratio of the amount of liquid at the upper end of the dividing wall (8) going to the enrichment section (10) and the stripping section (11) of the column, i.e. amount to the enrichment section (10):amount to the stripping section (11), is set in the range from 1:0.2 to 1:5, i.e. from 5 to 0.2, preferably in the range from 1:0.5 to 1:2, i.e. from 2 to 0.5. This is preferably effected by the liquid being collected at the upper end of the dividing wall and being introduced via a regulating or adjusting device in the abovementioned ratio into the enrichment section and stripping section, respectively, of the column. This ensures a lower energy consumption.

In a further preferred process variant, the ratio of the amount of the vapor streams at the lower end of the dividing wall (8) going to the stripping section (12) and the enrichment section (13) of the column can also be set in addition to or as an alternative to regulation of the ratio of amounts of liquid runback at the upper end of the dividing wall (8). This is preferably effected by selection of the separation-active internals and/or by the additional installation of pressure drop-generating internals, for example orifice plates, or by regulation of the amounts of the vapor streams.

In a preferred process variant, the amounts of the vapor streams going to the stripping section (12) and the enrichment section (13) of the column, i.e. amount to stripping section (12):amount to enrichment section (13), is set in a ratio in the range from 1:0.5 to 1:2.0, i.e. from 2 to 0.5, preferably in a ratio in the range from 1:0.9 to 1:1.5, i.e. from 1/0.9 to 1/1.5.

The process of the invention is preferably carried out at a pressure at the top of the column of from 20 mbar to 5 bar, preferably from 50 to 200 mbar.

The upper joint column region (9) is preferably provided with temperature regulation supplying a temperature signal which can originate from a single measurement point or averaged over a plurality of measurement points below the uppermost theoretical plate, preferably at the third theoretical plate counted from the top, and utilizing as manipulated variable the distillate flow, the reflux ratio or preferably the amount of runback.

This ensures stable operation of the column, resulting in a further improvement in the achievable product purity.

In a further process variant, the lower column region is, in addition or as an alternative, provided with temperature regulation supplying a temperature signal which can originate from a single measurement point or averaged over a plurality of measurement points above the bottommost theoretical plate, preferably at the second theoretical plate counted from the bottom, and utilizing the amount taken off at the bottom as manipulated variable. A further improvement in stable column operation is achieved by means of this additional measure. Furthermore, it is possible, in addition or as an alternative, to provide level regulation which utilizes the amount taken off at the side as manipulated variable at the bottom of the column.

The ratio of the cross-sectional areas of the region of the offtake section (11, 13) to the region of the inflow section (10, 12) is preferably from 4:1 to 1:4, particularly preferably from 1.5:1 to 1:1.5, e.g. 1:1.

The dividing wall column (1) has a number of theoretical plates in the range from 20 to 80. Separation-active internals are present in the joint upper column region (9) and in the joint lower column region (14) and also in the inflow section (10, 12) and offtake section (11, 13).

The indication of the number of theoretical plates of the dividing wall column (1) always relates to the sum of the theoretical plates in the joint upper column region (9), the joint lower column region (14) and the inflow section (10, 12).

In general, the number of theoretical plates in the offtake section (11, 13) is the same as in the inflow section (10, 12), but can also be greater, e.g. greater by a factor of from 1 to 5, or smaller, e.g. smaller by a factor of from 1 to 5.

The side feed point (2) for the crude butyl acrylate is arranged at a theoretical plate in the region commencing at least two theoretical plates above the bottommost theoretical plate and ending at least two theoretical plates below the uppermost theoretical plate, preferably at a theoretical plate in the region commencing at least five theoretical plates above the bottommost theoretical plate and ending at least five theoretical plates below the uppermost theoretical plate.

The side offtake point (3) for the pure butyl acrylate is arranged at a theoretical plate in the region commencing at least two theoretical plates above the bottommost theoretical plate and ending at least two theoretical plates below the uppermost theoretical plate, preferably in the region commencing at least five theoretical plates above the bottommost theoretical plate and ending at least five theoretical plates below the uppermost theoretical plate.

The dividing wall (8) is arranged in the column in the region commencing at least one theoretical plate above the bottommost theoretical plate and ending at least one theoretical plate below the uppermost theoretical plate, preferably in the region commencing at least four theoretical plates above the bottommost theoretical plate and ending at least four theoretical plates below the uppermost theoretical plate, particularly preferably in each case centrally.

In a particularly preferred embodiment, the dividing wall column (1) has a number of theoretical plates in the range from 30 to 40, the side feed point (2) for the crude butyl acrylate is arranged at a theoretical plate in the region commencing at least 20 theoretical plates above the bottommost theoretical plate and ending at least two theoretical plates below the uppermost theoretical plate, the side offtake point (3) for the pure butyl acrylate is arranged at a theoretical plate in the region commencing at least 10 theoretical plates above the bottommost theoretical plate and ending at least 10 theoretical plates below the uppermost theoretical plate and the dividing wall (8) in the column is arranged in the region commencing at least five theoretical plates above the bottommost theoretical plate and ending at least five theoretical plates below the uppermost theoretical plate.

In the case of equal numbers of theoretical plates in the offtake section (11, 13) and the feed section (10, 12), the side offtake point (3) can be located either at the same theoretical plate as the side feed point (2) or else below or above the side feed point; however self-evidently in each case on the other side of the dividing wall (8) (cf. FIG. 1); the opposite side offtake point (3) is preferably located below, e.g. from one to 25, in particular from 5 to 20, very particularly preferably from 10 to 18, theoretical plates below, the side feed point (2). (The theoretical plates in the column or in the column region concerned or in the column section concerned are always counted from the bottom upward.)

In the case of different numbers of theoretical plates in the feed section (11, 13) and the inflow section (10, 12), the side having the greater total number of theoretical plates in the region of the dividing wall (8) is employed for counting the number of theoretical plates for establishing the relative height position of feed point and offtake point.

There are in principle no restrictions in respect of the separation-active internals; preference is given to random packing elements and/or ordered packing and/or trays being provided.

The internals can in each case be selected individually for the column regions above and below (9, 14) the dividing wall and in the regions of the dividing wall (10, 11, 12, 13).

In a further preferred process variant, dual-flow trays are used as separation-active internals in the dividing wall column. The term dual-flow tray refers in a known manner to a column tray having openings through which vapor and liquid are passed in countercurrent.

In the thermal treatment of mixtures which comprise one or more polymerizable compounds in a column, there is always the problem that the column and the column internals are fouled by deposits and have to be cleaned in a complicated fashion, resulting in operation having to be interrupted. For the present purposes, the term thermal treatment refers to processes such as distillation or rectification, absorption, extraction or stripping. Mixtures which can be subjected to thermal treatment in a column are generally fluid, i.e. gaseous, liquid or gaseous/liquid.

The use of dual-flow trays reduces the fouling susceptibility of the dividing wall column compared to conventional tray columns. This increases the operating time of the column and thus makes it more economical.

Dual-flow trays are preferably used in the region of the dividing wall (10, 11, 12, 13); in a further preferred embodiment, dual-flow trays are also used in the joint upper column region (9) and in the joint lower column region (14).

A further advantageous embodiment provides for the use of dual-flow trays in the region of the dividing wall (10, 11, 12, 13) and in the joint lower column region (14) and also the use of random packing elements or ordered packing in the joint upper column region (9).

In WO 03/043712 A1 (BASF AG), it was shown for a conventional column without dividing wall that a considerable reduction in the fouling susceptibility and thus a considerably lengthening of the operating time of tray columns could be achieved by targeted selection of the diameters of the openings in the dual-flow trays.

In dividing wall columns, the same pressure drop prevails on both sides of the dividing wall. Precise setting of the gas distribution over the respective trays on the inflow side and on the offtake side by selection of the opening ratios of the trays on the inflow side and on the offtake side is of great advantage.

The gas distribution to the inflow side and the offtake side can be set precisely via targeted selection of the opening ratios. As a result of the different opening ratios of the dual-flow trays, different amounts of gas go to the two sides of the dividing wall at the same pressure drop. A complicated gas distribution facility below the dividing wall can thereby be dispensed with.

The opening ratio is set via the size and/or number of the openings. The opening ratio of a dual-flow tray is, as is known, the ratio of the sum of the areas of the openings and the total area of the dual-flow tray.

According to the invention, the openings of the dual-flow trays within a column can be made different, namely in that the diameter of the openings and/or the number of the openings are varied.

There is in principle no restriction in respect of the shape of the openings:

These can have any geometric shape, for example circles, ellipses, rectangles or polygons. The openings in the dual-flow trays are preferably circular.

A person skilled in the art can easily determine the required opening ratio as a function of gas and liquid loading and also opening diameter. The diameter of the openings in the dual-flow trays is preferably in the range from 10 to 80 mm, with dual-flow trays arranged above the feed point preferably having openings in the range from 10 to 50 mm and dual-flow trays arranged below the feed point, on the other hand, preferably having openings having diameters in the range from 15 to 80 mm.

The opening ratio of the dual-flow trays is preferably in the range from 10 to 30%.

In the process of the invention, the acrylic monomer, i.e. the butyl acrylate, is preferably stabilized by means of suitable polymerization inhibitors in order to avoid undesirable polymerization. That is to say, the process of the invention is preferably carried out in the presence of effective amounts of a stabilizer or a plurality of stabilizers. Suitable stabilizers are in principle all polymerization inhibitors which are recommended for stabilizing (meth)acrylic acid and (meth)acrylic esters in, for example, DE 10 2005 053 982 A1 (BASF AG) and DE 102 58 329 A1 (BASF AG).

Suitable stabilizers can be, for example, N oxides (nitroxyl or N-oxyl radicals, i.e. compounds which have at least one >N—O group), e.g. 4-hydroxy-2,2,6,6-tetramethylpiperidin-N-oxyl or 4-oxo-2,2,6,6-tetramethylpiperidin-N-oxyl, phenols and naphthols such as p-methoxyphenol, p-aminophenol, p-nitrosophenol, 2-tert-butylphenol, 4-tert-butylphenol, 2,4-di-tert-butylphenol, 2-methyl-4-tert-butylphenol, 2,6-tert-butyl-4-methylphenol or 4-tert-butyl-2,6-dimethylphenol, quinones such as hydroquinone or hydroquinone monomethyl ether, aromatic amines such as N,N-diphenylamine, phenylenediamines such as N,N'-dialkyl-p-phenylenediamine, where the alkyl radicals can be identical or different and can in each case have, independently of one another, from 1 to 4 carbon atoms and be linear or branched, e.g. N,N'-dimethyl-p-phenylenediamine or N,N'-diethyl-p-phenylenediamine, hydroxylamines such as N,N-diethylhydroxylamine, imines such as methylethylimine or methylene violet, sulfonamides such as N-methyl-4-toluenesulfonamide or N-tert-butyl-4-toluenesulfonamide, oximes such as aldoximes, ketoximes or amidoximes, e.g. diethyl ketoxime, methyl ethyl ketoxime or salicylaldoxime, phosphorus-comprising compounds such as triphenyl phosphine, triphenyl phosphite or triethyl phosphite, sulfur-comprising compounds such as diphenyl sulfide or phenothiazine, metal salts such as cerium(III) acetate or cerium (III) ethylhexanoate, or mixtures thereof.

The stabilization is preferably effected by means of phenothiazine (PTZ), p-methoxyphenol (MeHQ), hydroquinone, hydroquinone monomethyl ether, 4-hydroxy-2,2,6,6-tetramethylpiperidin-N-oxyl, 4-oxo-2,2,6,6-tetramethylpiperidin-N-oxyl, 2,6-tert-butyl-4-methylphenol or mixtures thereof.

Very particular preference is given to using phenothiazine (PTZ) and/or p-methoxyphenol (MeHQ) as polymerization inhibitor.

Even though the inhibitors can be added as pure substance, it is advantageous to add the inhibitor dissolved in a solvent as solution which can be metered in simply and reproducibly, with inhibitor mixtures in a single solution also being possible in principle. Preference is given to using a liquid which is in any case present in the acrylate synthesis process or the mixture of materials in the column as solvent. Particularly preferred choices for the solvent are the acrylate product itself (here n-butyl or isobutyl acrylate) or one of the starting materials for the synthesis of the acrylate (here acrylic acid or n-butanol or isobutanol).

The invention will be illustrated below with the aid of a drawing (FIG. 1) and an example.

The drawing shows, in the single figure, a dividing wall column 1 having a dividing wall 8 which divides the dividing wall column 1 into a joint upper column region 9, an inflow section 10 and 12 with enrichment section 10 and stripping section 12, an offtake section 11 and 13 with a stripping section 11 and an enrichment section 13, and also a joint lower column region 14. Separation-active internals are present in the column regions 9 and 14 and in the sections 10 to 13. The crude butyl acrylate 2 enters the dividing wall column 1 between the column sections 10 and 12. The pure butyl acrylate 3 is taken off between the column sections 11 and 13, preferably in liquid form. The vapor stream 15 obtained at the top of the column is partially condensed in the condenser 6, which is optionally supplemented by an after-condenser, and divided into the reflux stream 16 and the distillate stream 4. The uncondensed fraction from the condenser 6 comprises the low-boiling impurities and is taken off in vapor form as stream 19. At the lower end of the column, the liquid 17 is partially vaporized in a vaporizer 7 and recirculated via the pipe 18 into the column. A substream 5, which comprises the relatively high-boiling impurities, is taken off. The vaporizer 7 can be configured as a natural convection vaporizer or as forced circulation vaporizer; in the latter case, a circulation pump for the liquid stream 17 is additionally required. To avoid undesirable polymerization reactions, it is particularly advantageous to use a falling film evaporator instead of the forced circulation vaporizer since the shortest residence times are possible using such a falling film evaporator. To reduce the residence time of the liquid in the vaporizer system, it is advantageous to arrange the level regulation not in the lower column cap but instead in the feed conduit for the liquid 17.

Figure 2:
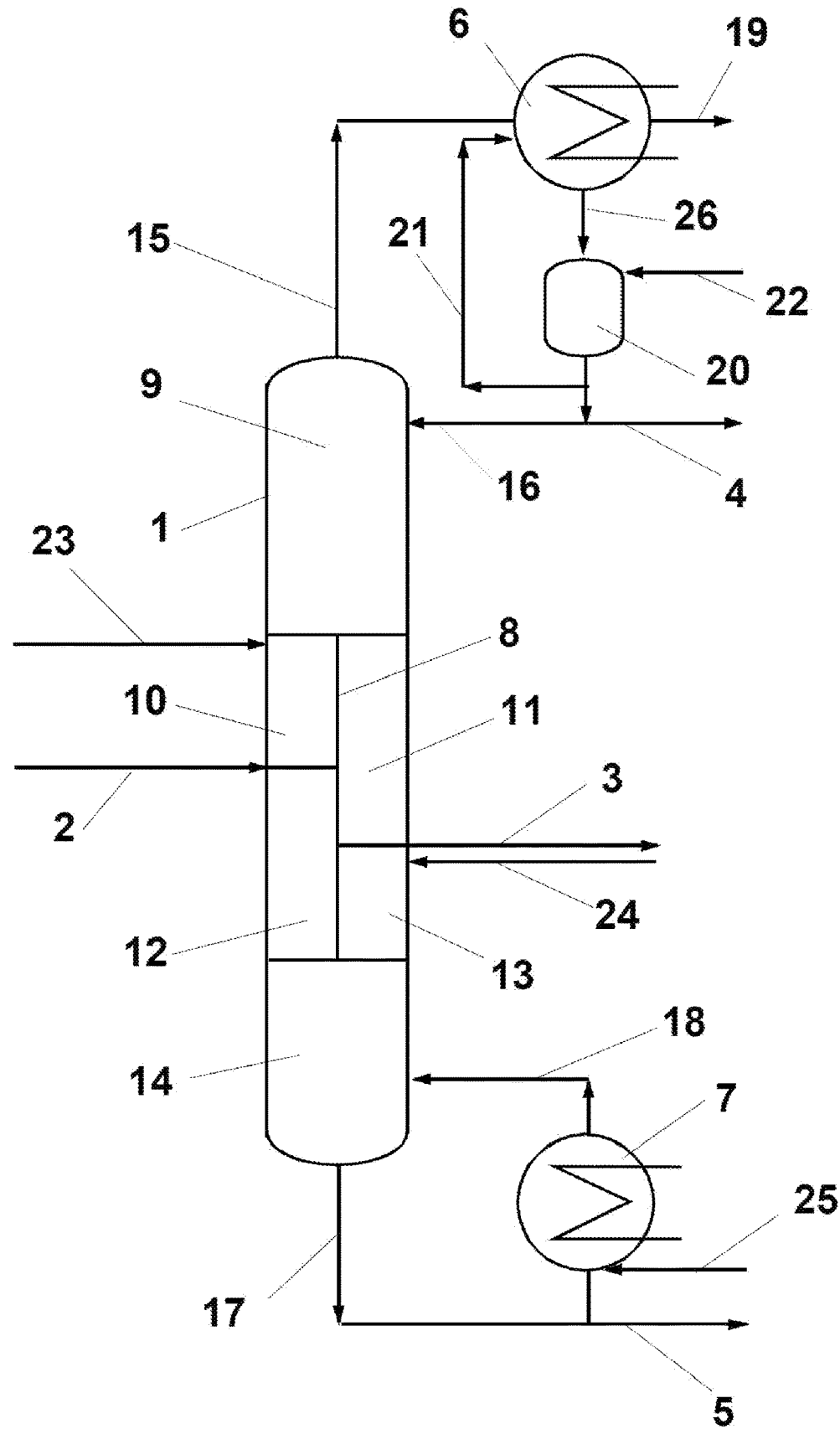
FIG. 2 shows a preferred mode of operation of a dividing wall column.

In a preferred mode of operation (cf. FIG. 2), a stabilizer 1 (23) (process stabilizer; e.g. in particular PTZ) is introduced into the enrichment section (10) of the inflow section (10, 12), there in particular just below the upper end of the dividing wall (8), in the process of the invention. The stabilizer 1 can, in particular, be used as a solution in a suitable solvent, particularly a solvent as indicated above, e.g. n-butyl acrylate or isobutyl acrylate. In this way, the entire inflow section (10, 12) and the joint lower part of the column (14) is stabilized by means of the process stabilizer. ("Just below the upper end of the dividing wall (8)" means, for example, "from one to 5 theoretical plates below the upper end of the dividing wall (8)").

Furthermore (cf. FIG. 2), a stabilizer 2 (22) (known as storage stabilizer, e.g. in particular MeHQ) is preferably introduced into the container (20) which collects the condensate (26) and/or into the conduit of a quenching circuit (21) and/or at the top of the condenser (6) in the process of the invention. The quenching circuit which is preferably provided (i.e. the liquid return stream of part of the condensate, e.g. from 10 to 50 hundredths by weight of the condensate, into the condenser (6)) has the function of particularly satisfactorily stabilizing the naturally stabilizer-free vapors (15) during condensation in the condenser (6). The joint upper column region (9) above the dividing wall (8) and also the feed section (10, 12) and offtake section (11, 13) in the region of the dividing wall are then stabilized by means of the stabilizer (in particular MeHQ) via the return line (16), with oxygen originating from lean air also being present. The introduction of lean air (25) (mixture of air and nitrogen, in particular in such a way that an oxygen content of from 4 to 9% by volume results) occurs in particular either at the lower end of the vaporizer (7) or at the lower end of the column (1).

In a further process variant (cf. FIG. 2), process stabilizer (24), in particular PTZ, is additionally introduced into the enrichment section (13) below the side offtake point (3).

All pressures indicated are absolute pressures.

All amounts in ppm are by weight (ppm by weight).

A "low boiler" (relative to butyl acrylate) is a material whose boiling point is lower than the boiling point of the butyl acrylate concerned, i.e. n-butyl acrylate or isobutyl acrylate, at the same pressure.

A "relatively high boiler" (relative to butyl acrylate) is a material whose boiling point is higher than the boiling point of the butyl acrylate concerned, i.e. n-butyl acrylate or isobutyl acrylate, at the same pressure.

EXAMPLES

The modes of operation are presented with the aid of data from a thermodynamic simulation of an overall plant for preparing n-butyl acrylate.

The thermodynamic simulation of the process was carried out using the software Aspen Plus® (Aspen for short). Aspen is comprehensive simulation software which is used for the modeling, simulation and optimization of chemical processes and plants in industry. Aspen has comprehensive modeling data banks for modeling the basic operations and also materials data banks for the materials properties of many different substances. The properties of mixtures are calculated by Aspen by means of various thermodynamic models from the materials data of the pure substances.

Example 1

(Ratio of amount of liquid at the upper end of the dividing wall (8), enrichment section (10):stripping section (11)=1:2 and ratio of amount of the vapor streams at the lower end of the dividing wall (8), stripping section (12):enrichment section (13)=1:1)

A crude n-butyl acrylate stream of 16 000 kg/h having a temperature of 70° C. was fed in in liquid form at the 28th theoretical plate of a dividing wall column (1) having a total of 35 theoretical plates. The crude n-butyl acrylate had the following composition:

| | |
|---|---|
| n-Butyl acrylate: | 86.4% by weight |
| Water: | 1.1% by weight |
| n-Butanol: | 3.7% by weight |
| Di-n-butyl ether: | 0.33% by weight |
| n-Butyl acetate: | 2.2% by weight |
| Butoxy ester: | 5.0% by weight |

Further relatively high boilers (relative to n-butyl acrylate): balance

The dividing wall (8) extended from the 6th to the 30th theoretical plate. The side offtake (3) was located at the 15th theoretical plate. The column was operated at a pressure at the top of 100 mbar and a pressure at the bottom of 240 mbar.

At the top of the column condensation was carried out at a temperature of 35° C. A gaseous low boiler-comprising stream (19) of 19 kg/h was taken off from the condenser (6). A substream (4) of 1423 kg/h was taken off from the condensed stream. The high-boiling impurities (5) were taken off at the bottom of the column at a flow rate of 1836 kg/h and a temperature of 117° C. At the side offtake, the desired product pure butyl acrylate was obtained in liquid form at a temperature of 94° C. in an amount of 12 722 kg/h.

The side offtake stream (3) had the following composition:

| | |
|---|---|
| n-Butyl acrylate: | 99.91% by weight |
| Water: | <0.01% by weight |
| n-Butanol: | <0.01% by weight |
| Di-n-butyl ether: | 643 ppm by weight |
| n-Butyl acetate: | 100 ppm by weight |

Further relatively high boilers (relative to n-butyl acrylate): balance

The minimum content of acrylate of >99.5% by weight and the commercial specifications for the secondary components n-butyl acetate at 100 ppm and for di-n-butyl ether at 1000 ppm are adhered to. The distillation yield for n-butyl acrylate was more than 92%.

The ratio of amounts of liquid for the liquid at the upper end of the dividing wall (8), enrichment section (10): stripping section (11), was 1:2. At the lower end of the dividing wall (8), the amounts of vapor stream, stripping section (12):enrichment section (13), were divided in the ratio 1:1. The heating power of the vaporizer was 3224 kW.

The process of the invention enabled the distillation of crude butyl acrylate to give pure butyl acrylate to be carried out, for example, at an annual capacity of 100 000 metric tons while adhering to the required specifications with a capital cost saving of 25% and an energy cost saving of 31% compared to a conventional two-stage distillation process.

Comparative Example 1

(Ratio of amount of liquid at the upper end of the dividing wall (8), enrichment section (10):stripping section (11)=1:7)

A crude n-butyl acrylate stream of 16 000 kg/h having a temperature of 70° C. was fed in in liquid form at the 28th theoretical plate of a dividing wall column (1) having a total of 35 theoretical plates. The crude n-butyl acrylate had the following composition:

| | |
|---|---|
| n-Butyl acrylate: | 86.4% by weight |
| Water: | 1.1% by weight |
| n-Butanol: | 3.7% by weight |
| Di-n-butyl ether: | 0.33% by weight |
| n-Butyl acetate: | 2.2% by weight |
| Butoxy ester: | 5.0% by weight |

Further relatively high boilers (relative to n-butyl acrylate): balance

The dividing wall (8) extended from the 6th to the 30th theoretical plate. The side offtake (3) was located at the 15th theoretical plate. The column was operated at a pressure at the top of 100 mbar and a pressure at the bottom of 240 mbar.

At the top of the column, condensation was carried out at a temperature of 35° C. A gaseous low boiler-comprising stream (19) of 19 kg/h was taken off from the condenser (6). A substream (4) of 1411 kg/h was taken off from the condensed stream. The high-boiling impurities (5) were taken off at the bottom of the column at a flow rate of 1850 kg/h and a temperature of 117° C. At the side offtake, the desired product pure butyl acrylate was obtained in liquid form at a temperature of 94° C. in an amount of 12 720 kg/h.

The side offtake stream (3) had the following composition:

| | |
|---|---|
| n-Butyl acrylate: | 99.83% by weight |
| Water: | <0.01% by weight |
| n-Butanol: | <0.01% by weight |
| Di-n-butyl ether: | 1212 ppm by weight |
| n-Butyl acetate: | 258 ppm by weight |
| Butoxy ester: | <0.01% by weight |

Further relatively high boilers (relative to n-butyl acrylate): balance

The minimum content of acrylate of >99.5% by weight is adhered to but the commercial specifications for the secondary components n-butyl acetate at 100 ppm and for di-n-butyl ether at 1000 ppm are not adhered to.

The distillation yield for n-butyl acrylate was more than 91%.

The ratio of amounts of liquid for the liquid at the upper end of the dividing wall (8), enrichment section (10): stripping section (11), was 1:7. At the lower end of the dividing wall (8), the amounts of vapor stream, stripping section (12):enrichment section (13), were divided in the ratio 1:1. The heating power of the vaporizer was 4524 kW.

Comparative Example 2

(Ratio of amounts of the vapor streams at the lower end of the dividing wall (8), stripping section (12):enrichment section (13)=3:1)

A crude n-butyl acrylate stream of 16 000 kg/h having a temperature of 70° C. was fed in in liquid form at the 28th theoretical plate of a dividing wall column (1) having a total of 35 theoretical plates. The crude n-butyl acrylate had the following composition:

| | |
|---|---|
| n-Butyl acrylate: | 86.4% by weight |
| Water: | 1.1% by weight |
| n-Butanol: | 3.7% by weight |
| Di-n-butyl ether: | 0.33% by weight |
| n-Butyl acetate: | 2.2% by weight |
| Butoxy ester: | 5.0% by weight |

Further relatively high boilers (relative to n-butyl acrylate): balance

The dividing wall (8) extended from the 6th to the 30th theoretical plate. The side offtake (3) was located at the 15th theoretical plate. The column was operated at a pressure at the top of 100 mbar and a pressure at the bottom of 240 mbar.

At the top of the column, condensation was carried out at a temperature of 35° C. A gaseous low boiler-comprising stream (19) of 18 kg/h was taken off from the condenser (6). A substream (4) of 1236 kg/h was taken off from the condensed stream. The high-boiling impurities (5) were taken off at the bottom of the column at a flow rate of 2026 kg/h and a temperature of 115° C. At the side offtake, the desired product pure butyl acrylate was obtained in liquid form at a temperature of 93° C. in an amount of 12 720 kg/h.

The side offtake stream (3) had the following composition:

| | |
|---|---|
| n-Butyl acrylate: | 98.75% by weight |
| Water: | <0.01% by weight |
| n-Butanol: | <0.4% by weight |
| Di-n-butyl ether: | 1798 ppm by weight |
| n-Butyl acetate: | 6640 ppm by weight |
| Butoxy ester: | <0.01 ppm by weight |

Further relatively high boilers (relative to n-butyl acrylate): balance

The minimum content of acrylate of >99.5% by weight and the commercial specifications for the secondary components n-butyl acetate at 100 ppm and for di-n-butyl ether at 1000 ppm are not adhered to.

The distillation yield for n-butyl acrylate was more than 90%.

The ratio of amounts of liquid for the liquid at the upper end of the dividing wall (8), enrichment section (10): stripping section (11), was 1:2. At the lower end of the dividing wall (8), the amounts of vapor stream, stripping section (12):enrichment section (13), were divided in the ratio 3:1. The heating power of the vaporizer was 3824 kW.

The invention claimed is:

1. A process, comprising isolating pure butyl acrylate from a crude butyl acrylate, where butyl is n-butyl or isobutyl, by distillation, wherein:
   the butyl acrylate is obtained from reacting butanol and acrylic acid,
   the process is carried out in a dividing wall column which has separation-active internals and a vaporizer and in which a dividing wall is arranged in a longitudinal direction of the column to form an upper joint column region, a lower joint column region, an inflow section having a side feed point and an offtake section having a side offtake point;
   the column has 20 to 80 theoretical plates in the joint upper column region, the joint lower column region and the inflow section;
   the side feed point for the crude butyl acrylate is arranged at a theoretical plate in a region commencing at least two theoretical plates above a bottommost theoretical plate and ending at least two theoretical plates below an uppermost theoretical plate;
   the side offtake point for the pure butyl acrylate is arranged at a theoretical plate in the region commencing at least two theoretical plates above the bottommost theoretical plate and ending at least two theoretical plates below the uppermost theoretical plate;
   the dividing wall is arranged in the column in the region commencing at least one theoretical plate above the bottommost theoretical plate and ending at least one theoretical plate below the uppermost theoretical plate;
   the ratio of an amount of liquid at an upper end of the dividing wall going to an enrichment section and a stripping section of the column is set in the range from 1:0.2 to 1:5;
   the ratio of an amount of vapor streams at a lower end of the dividing wall going to the stripping section and the enrichment section of the column is set in a range from 1:0.5 to 1:2.0,
   dual-flow trays are provided as separation-active internals; and
   the dual-flow trays on the inflow side and offtake side have different opening ratios for setting an optimal gas distribution over the two sides of the dividing wall.

2. The process according to the claim 1, wherein:
   the side feed point for the crude butyl acrylate is arranged at a theoretical plate in a region commencing at least five theoretical plates above the bottommost theoretical plate and ending at least five theoretical plates below the uppermost theoretical plate;
   the side offtake point for the pure butyl acrylate is arranged at a theoretical plate in the region commencing at least five theoretical plates above the bottommost theoretical plate and ending at least five theoretical plates below the uppermost theoretical plate; and
   the dividing wall in the column is arranged in a region commencing at least four theoretical plates above the bottommost theoretical plate and ending at least four theoretical plates below the uppermost theoretical plate.

3. The process according to claim 1, wherein:
   the column has 30 to 40 theoretical plates;
   the side feed point for the crude butyl acrylate is arranged at a theoretical plate in a region commencing at least 20 theoretical plates above the bottommost theoretical plate and ending at least two theoretical plates below the uppermost theoretical plate;
   the side offtake point for the pure butyl acrylate is arranged at a theoretical plate in a region commencing at least 10 theoretical plates above the lowermost theoretical plate and ending at least 10 theoretical plates below the uppermost theoretical plate; and
   the dividing wall in the column is arranged in a region commencing at least five theoretical plates above the bottommost theoretical plate and ending at least five theoretical plates below the uppermost theoretical plate.

4. The process according to claim 1, wherein the side offtake point is located at least one theoretical plate below the side feed point, where in the case of different numbers of theoretical plates in the offtake section and the inflow section, the side having the greatest total number of theoretical plates in the region of the dividing wall is employed for counting the number of theoretical plates for determining the relative height position of feed point and offtake point.

5. The process according to claim 1, wherein the residence time in the vaporizer and the associated piping system is limited to from 1 to 60 minutes.

6. The process according to claim 1, wherein the ratio of amounts of liquid at the upper end of the dividing wall going to the enrichment section and the stripping section of the column is set in the range from 1:0.5 to 1:2.

7. The process according to claim 1, wherein the ratio of amounts of the vapor streams at the lower end of the dividing wall going to the stripping section and the enrichment section of the column is set in the range from 1:0.9 to 1:1.5.

8. The process according to claim 1, wherein a pressure at the top of the column is in the range from 20 mbar to 5 bar.

9. The process according to claim 1, wherein there is temperature regulation in the upper joint column region using a temperature signal below the uppermost theoretical plate, which utilizes distillate flow, reflux ratio or reflux amount as a manipulated variable.

10. The process according to claim 1, wherein there is temperature regulation in the lower joint column region using a temperature signal above the bottommost theoretical plate, which utilizes the amount taken off at the bottom as a manipulated variable.

11. The process according to claim 1, wherein there is level regulation at the bottom of the column which utilizes the amount taken off at the side as a manipulated variable.

12. The process according to claim 1, wherein the ratio of cross-sectional areas of the region of the offtake section to a region of the inflow section is from 4:1 to 1:4.

13. The process according to claim 1, wherein the ratio of cross-sectional areas of the region of the offtake section to the region of the inflow section is from 1.5:1 to 1:1.5.

14. The process according to claim 1, which the pure butyl acrylate is isolated with a purity of ≥98.5% by weight by distillation.

15. The process according to claim 1, wherein the butyl acrylate is n-butyl acrylate.

16. The process according to claim 1, wherein the butyl acrylate is isobutyl acrylate.

17. The process according to claim 15, wherein the crude n-butyl acrylate has the following composition:
from 40 to 90% by weight of n-butyl acrylate,
from 0.1 to 20% by weight of n-butanol,
from 0.1 to 20% by weight of water,
from 0.1 to 20% by weight of relatively high boilers (relative to n-butyl acrylate), and
from 0.1 to 20% by weight of further low boilers (relative to n-butyl acrylate).

18. The process according to claim 16, wherein the crude isobutyl acrylate has the following composition:
from 40 to 90% by weight of isobutyl acrylate,
from 0.1 to 20% by weight of isobutanol,
from 0.1 to 20% by weight of water,
from 0.1 to 20% by weight of relatively high boilers (relative to isobutyl acrylate), and
from 0.1 to 20% by weight of further low boilers (relative to isobutyl acrylate).

19. The process according to claim 1, wherein a first stabilizer is introduced into the enrichment section of the inflow section.

20. The process according to claim 19, wherein the first stabilizer is phenothiazine (PTZ).

21. The process according to claim 1, wherein a second stabilizer is introduced into the container which collects a condensate and/or into a conduit of a quenching circuit, where this is a liquid return stream of part of the condensate into the condenser and/or at a top of the condenser.

22. The process according to claim 21, wherein the second stabilizer is p-methoxyphenol (MeHQ).

* * * * *